(12) United States Patent
Hyde

(10) Patent No.: US 10,521,982 B2
(45) Date of Patent: Dec. 31, 2019

(54) SENSING TUBE DIAGNOSTIC SYSTEMS AND METHODS

(71) Applicant: GM Global Technology Operations LLC, Detroit, MI (US)

(72) Inventor: Amanda Hyde, Warren, MI (US)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 190 days.

(21) Appl. No.: 15/873,086

(22) Filed: Jan. 17, 2018

(65) Prior Publication Data

US 2019/0221056 A1 Jul. 18, 2019

(51) Int. Cl.
| | | |
|---|---|---|
| *G07C 5/08* | (2006.01) | |
| *B60Q 9/00* | (2006.01) | |
| *B60R 21/38* | (2011.01) | |
| *G01L 13/02* | (2006.01) | |
| *G01L 15/00* | (2006.01) | |
| *G01L 27/00* | (2006.01) | |
| B60R 21/0136 | (2006.01) | |
| G01N 3/30 | (2006.01) | |

(Continued)

(52) U.S. Cl.
CPC .............. *G07C 5/0808* (2013.01); *B60Q 9/00* (2013.01); *B60R 21/38* (2013.01); *G01L 13/021* (2013.01); *G01L 15/00* (2013.01); *G01L 27/007* (2013.01); *B60R 19/023* (2013.01); *B60R 19/18* (2013.01); *B60R 19/483* (2013.01); *B60R 21/0136* (2013.01); *B60R 21/34* (2013.01); *B60Y 2400/306* (2013.01); *G01N 3/30* (2013.01)

(58) Field of Classification Search
CPC ....... B60R 19/483; B60R 19/48; B60R 21/34; B60R 21/0136; B60R 19/18; B60R 19/34; B60R 21/38; B60R 19/023; B29C 51/10; C07D 207/452; H02K 7/1853; H02K 35/02; H02K 7/1876; G07C 5/0808; G01L 5/0052; G01L 13/021; G01L 15/00; G01L 27/007; G01N 3/30; C08J 3/243; C08K 5/39; C08L 23/0815; C25B 1/10; C25B 9/08; C25B 15/08; C25B 9/04; C23F 13/005; F03B 13/16; F03B 13/20; H02M 7/064; B60Y 2400/306
See application file for complete search history.

(56) References Cited

U.S. PATENT DOCUMENTS

2014/0312636 A1\* 10/2014 Corwin .................... B60R 21/34
293/133
2015/0274119 A1\* 10/2015 Schondorf ............ B60R 19/483
293/132

(Continued)

*Primary Examiner* — Behrang Badii

(57) ABSTRACT

A diagnostic system of a vehicle includes an energy absorber sandwiched between a front bumper fascia and a front bumper reinforcement of the vehicle. A sensing tube is located between a portion of the energy absorber and the front bumper reinforcement. A first pressure sensor and a second pressure sensor measure a first pressure of air and a second pressure of air within the sensing tube, respectively. An actuator is configured to actuate and vary a pressure within the sensing tube. A diagnostic module is configured to selectively diagnose the presence of a fault with the sensing tube based on at least one of: a first change in the first pressure in response to actuation of the actuator; and a second change in the second pressure in response to the actuation of the actuator.

20 Claims, 12 Drawing Sheets

(51) Int. Cl.
    *B60R 19/48*     (2006.01)
    *B60R 21/34*     (2011.01)
    *B60R 19/18*     (2006.01)
    *B60R 19/02*     (2006.01)

(56) References Cited

U.S. PATENT DOCUMENTS

| | | | |
|---|---|---|---|
| 2016/0101753 A1* | 4/2016 | Higashimachi | B60R 19/023 |
| | | | 293/117 |
| 2018/0051226 A1* | 2/2018 | De Patto | C10M 147/04 |
| 2018/0079381 A1* | 3/2018 | Nakane | B60R 19/483 |

* cited by examiner

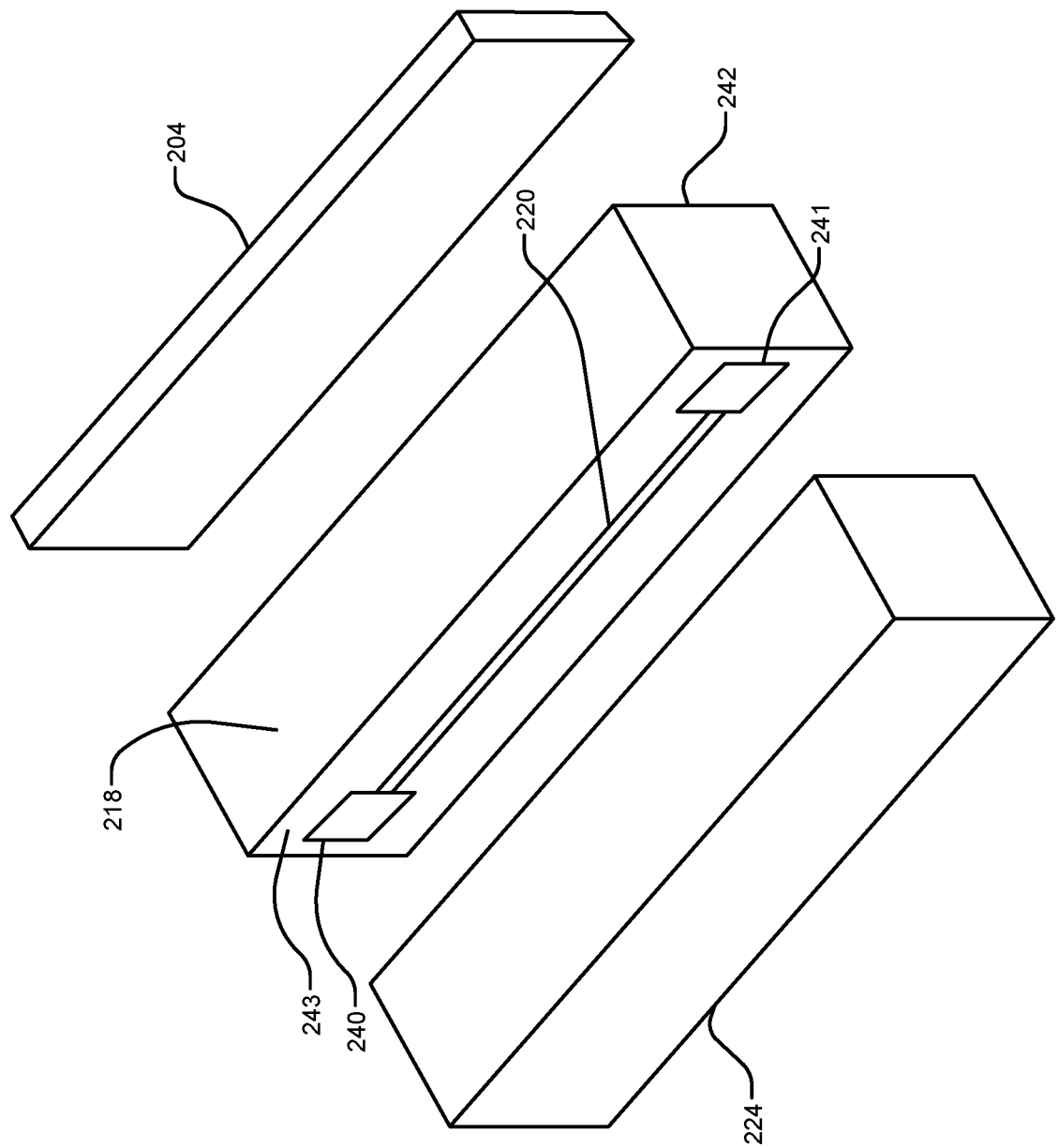

SENSING TUBE DIAGNOSTIC SYSTEMS AND METHODS

INTRODUCTION

The information provided in this section is for the purpose of generally presenting the context of the disclosure. Work of the presently named inventors, to the extent it is described in this section, as well as aspects of the description that may not otherwise qualify as prior art at the time of filing, are neither expressly nor impliedly admitted as prior art against the present disclosure.

The present disclosure relates to vehicles and more particularly systems and methods for diagnosing faults in sensing tubes of pedestrian protection systems.

Vehicles often include a number of different occupant protection systems. Examples of occupant protection systems include seat belts, air bags, etc. that protect occupants of a vehicle. Air bags may be provided at one or more locations within a vehicle.

Vehicles also include front and rear bumper reinforcements. The front and rear bumper reinforcements of a vehicle are attached to a chassis of the vehicle. The front and rear bumper reinforcements may be covered from external view by bumper covers, which can also be referred to as fascia. Energy absorbing material, such as energy absorbing foam, may be implemented between a bumper reinforcement and a bumper cover.

SUMMARY

In a feature, a diagnostic system of a vehicle is described. An energy absorber is sandwiched between a front bumper fascia and a front bumper reinforcement of the vehicle. A sensing tube is located between a portion of the energy absorber and the front bumper reinforcement. A first pressure sensor is connected to a first end of the sensing tube and is configured to measure a first pressure of air within the sensing tube. A second pressure sensor is connected to a second end of the sensing tube and is configured to measure a second pressure of air within the sensing tube. An actuator is configured to actuate and vary a pressure within the sensing tube. A diagnostic module is configured to selectively diagnose the presence of a fault with the sensing tube based on at least one of: a first change in the first pressure in response to actuation of the actuator; and a second change in the second pressure in response to the actuation of the actuator.

In further features, the diagnostic module is configured to diagnose the presence of the fault with the sensing tube when at least one of: the first change in the first pressure in response to actuation of the actuator is less than a predetermined pressure; and the second change in the second pressure in response to the actuation of the actuator is less than the predetermined pressure.

In further features, the diagnostic module is configured to diagnose that the fault is not present with the sensing tube when both: the first change in the first pressure in response to actuation of the actuator is greater than the predetermined pressure; and the second change in the second pressure in response to the actuation of the actuator is greater than the predetermined pressure.

In further features, the actuator comprises a piezoelectric tube actuator that surrounds a circumference of the sensing tube.

In further features, the actuator comprises a nitinol wire wrapped around a circumference of the sensing tube.

In further features, the actuator comprises a linear actuator that is configured to actuate and apply force to a side of the sensing tube.

In further features, the diagnostic system further includes a splitter, where the actuator comprises a linear actuator that includes a piston and that is connected to the splitter, and where the linear actuator is configured to extend the piston within the sensing tube.

In further features, the sensing tube is located within a recess in the energy absorber.

In further features, the sensing tube is located within a recess formed in a face of the energy absorber that faces the front bumper reinforcement.

In further features, the first and second pressure sensors include holes venting the sensing tube to ambient air.

In further features, the diagnostic system further includes an actuator control module configured to selectively lift a rear portion of a hood of the vehicle based on at least one of the first pressure measured by the first pressure sensor and the second pressure measured by the second pressure sensor.

In further features, the actuator control module is configured to disable the lifting of the rear portion of a hood of the vehicle when the fault is present with the sensing tube.

In further features, the diagnostic module is configured to diagnose that the fault is not present with the sensing tube when both: a first change in the first pressure in response to actuation of the actuator is greater than a first predetermined pressure; and a second change in the second pressure in response to the actuation of the actuator is greater than the first predetermined pressure; and the actuator control module is configured to lift the rear portion of the hood when both: a third change in the first pressure is greater than a second predetermined pressure; and a fourth change in the second pressure in response to the actuation of the actuator is greater than the second predetermined pressure.

In further features, the second predetermined pressure is greater than the first predetermined pressure.

In further features, the diagnostic module is configured to diagnose that the fault is present with the sensing tube when at least one of: the first change in the first pressure in response to actuation of the actuator is less than the first predetermined pressure; and the second change in the second pressure in response to the actuation of the actuator is less than the first predetermined pressure.

In further features, the diagnostic module is configured to store a predetermined diagnostic trouble code in memory when the fault is present with the sensing tube.

In further features, the diagnostic module is configured to display a malfunction indicator on a display of the vehicle or to illuminate a malfunction indicator light when the fault is present with the sensing tube.

In further features, the actuator is configured to actuate and increase the pressure within the sensing tube.

In a feature, a diagnostic method includes: by a first pressure sensor, measuring a first pressure of air within a sensing tube, where the sensing tube is located between a portion of an energy absorber and a front bumper reinforcement, and where the energy absorber is sandwiched between a front bumper fascia and the front bumper reinforcement; by a second pressure sensor, measuring a second pressure of air within the sensing tube; actuating and actuator and varying a pressure within the sensing tube; and selectively diagnosing the presence of a fault with the sensing tube based on at least one of: a first change in the first pressure in response to actuation of the actuator; and a second change in the second pressure in response to the actuation of the actuator.

In a feature, a diagnostic system of a vehicle includes a sensing tube. A first pressure sensor is connected to a first end of the sensing tube and is configured to measure a first pressure of air within the sensing tube. A second pressure sensor is connected to a second end of the sensing tube and is configured to measure a second pressure of air within the sensing tube. An actuator is configured to actuate and vary a pressure within the sensing tube. A diagnostic module is configured to selectively diagnose the presence of a fault with the sensing tube based on at least one of: a first change in the first pressure in response to actuation of the actuator; and a second change in the second pressure in response to the actuation of the actuator.

Further areas of applicability of the present disclosure will become apparent from the detailed description, the claims and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein:

FIG. 5 includes an exploded view of an example pedestrian protection system;

In the drawings, reference numbers may be reused to identify similar and/or identical elements.

DETAILED DESCRIPTION

Figure 1:
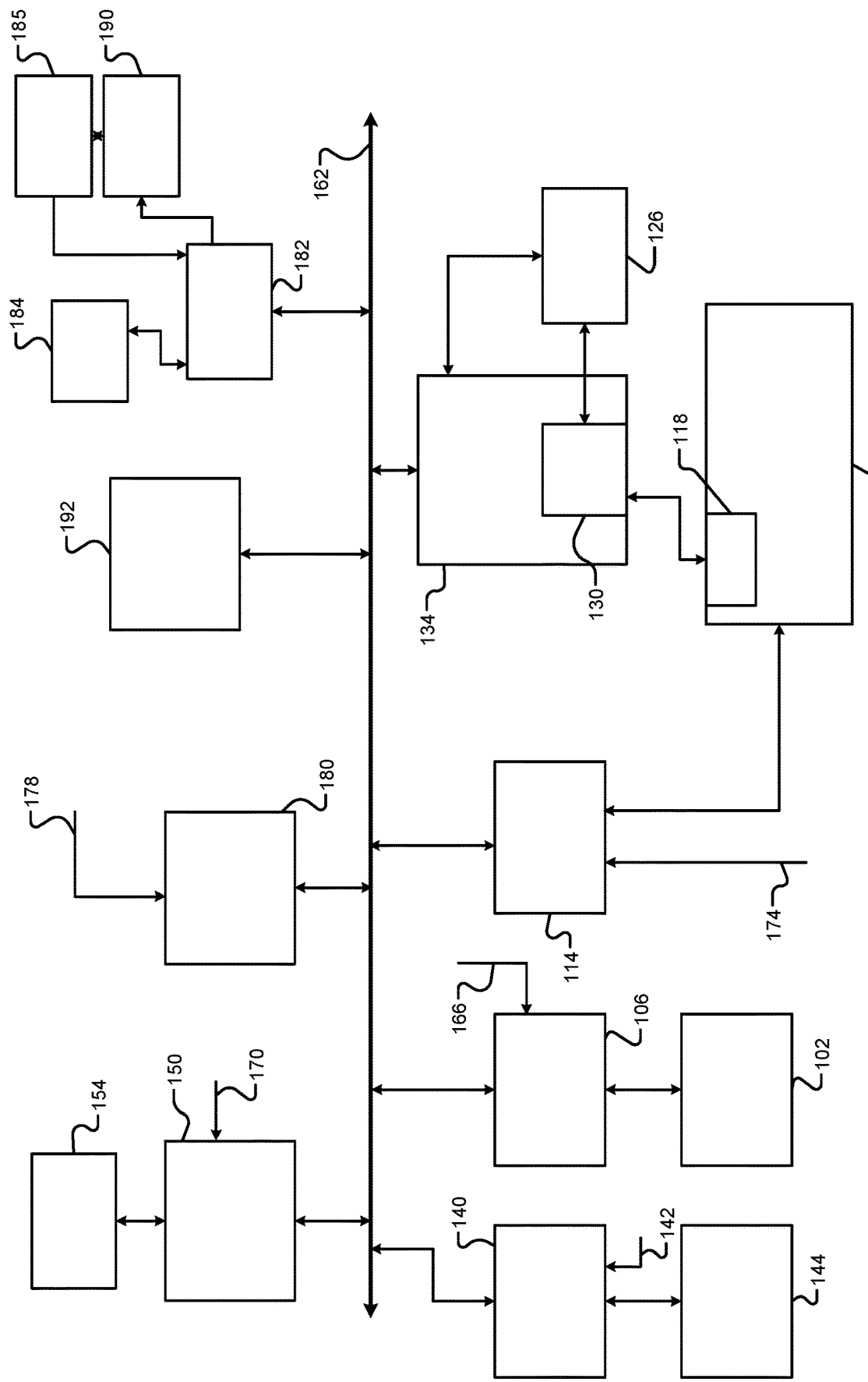
FIG. 1 is a functional block diagram of an example vehicle system.

A vehicle includes a front bumper fascia, an energy absorbing block, a front bumper reinforcement, and a pedestrian protection system. The front bumper reinforcement is attached to a chassis of the vehicle. The energy absorbing block is implemented between the front bumper reinforcement and the front bumper fascia. The front bumper fascia is a front bumper cover and covers the energy absorbing block and the front bumper reinforcement from view.

The pedestrian protection system includes a sensing tube, such as a sensing tube embedded in the energy absorbing block. First and second pressure sensors measure first and second pressures within the sensing tube. The sensing tube or the first and second pressure sensors include one or more vent holes such that pressure within the sensing tube can approach or reach ambient pressure.

When a collision with the front bumper fascia occurs, the sensing tube is compressed, such as against the front bumper reinforcement. The first and second pressures measured by the first and second pressure sensors therefore increase when a collision with the front bumper fascia occurs.

A pedestrian protection module determines whether the vehicle collided with a pedestrian, a vehicle, or another type of object based on changes in the first and second pressures measured by the first and second pressure sensors. The pedestrian protection module may actuate one or more actuators that lift a hood of the vehicle when a collision with a pedestrian is detected. Additionally or alternatively, the pedestrian protection module may deploy a windshield airbag when a collision with a pedestrian is detected.

Under some circumstances, however, the sensing tube may be damaged or may be disconnected from at least one of the first pressure sensor and the second pressure sensor. Because the sensing tube is vented to ambient pressure, damage of the sensing tube (e.g., puncturing, severing) and disconnection from at least one of the first pressure sensor and the second pressure sensor may not be detected as the first and second pressure sensors may properly measure ambient pressure.

According to the present disclosure, a diagnostic module diagnoses the presence of a fault with the sensing tube, such as damage of the sensing tube or disconnection of at least one of the first and second pressure sensors from the sensing tube. The diagnostic module selectively actuates an actuator to change (e.g., increase) pressure within the sensing tube. The actuator may be, for example, a linear actuator or a piezoelectric actuator.

The diagnostic module determines whether a fault is present with the sensing tube based on changes in the first and second pressures in response to the actuation of the actuator. For example, the diagnostic module may determine that the fault is not present with the sensing tube when the first and second pressures increase at least a predetermined amount in response to the actuation of the actuator. The diagnostic module may determine that the fault is present with the sensing tube when at least one of the first and second pressures does not increase by at least the predetermined amount in response to the actuation of the actuator and/or at least one of the first and second pressures too quickly returns to ambient pressure after the actuation of the actuator given the sizes of the one or more vent holes.

Referring now to FIG. 1, a functional block diagram of an example vehicle system is presented. While a vehicle system for a hybrid vehicle is shown and will be described, the present disclosure is also applicable to non-hybrid vehicles, electric vehicles, fuel cell vehicles, autonomous vehicles, semi-autonomous vehicles, non-autonomous vehicles, and other types of vehicles.

An engine 102 combusts an air/fuel mixture to generate drive torque. An engine control module (ECM) 106 controls the engine 102 based on a torque request, such as a torque request determined based on one or more driver inputs. For example, the ECM 106 may control actuation of engine actuators, such as a throttle valve, one or more spark plugs, one or more fuel injectors, valve actuators, camshaft phasers, an exhaust gas recirculation (EGR) valve, one or more boost devices, and other suitable engine actuators.

The engine 102 may output torque to a transmission 110. A transmission control module (TCM) 114 controls operation of the transmission 110. For example, the TCM 114 may control gear selection within the transmission 110 and one or more torque transfer devices (e.g., a torque converter, one or more clutches, etc.).

The vehicle system may include one or more electric motors. For example, an electric motor 118 may be implemented within the transmission 110 as shown in the example of FIG. 1. An electric motor can act as either a generator or as a motor at a given time. When acting as a generator, an electric motor converts mechanical energy into electrical energy. The electrical energy can be, for example, used to charge a battery 126 via a power control device (PCD) 130. When acting as a motor, an electric motor generates torque that may be used, for example, to supplement or replace torque output by the engine 102. While the example of one electric motor is provided, the vehicle may include zero or more than one electric motor.

A power inverter control module (PIM) 134 may control the electric motor 118 and the PCD 130. The PCD 130 applies (e.g., direct current) power from the battery 126 to the (e.g., alternating current) electric motor 118 based on signals from the PIM 134, and the PCD 130 provides power output by the electric motor 118, for example, to the battery 126. The PIM 134 may be referred to as a power inverter module (PIM) in various implementations.

A steering control module 140 controls steering/turning of wheels of the vehicle, for example, based on driver turning of a steering wheel within the vehicle and/or steering commands from one or more vehicle modules. A steering wheel angle sensor (SWA) monitors rotational position of the steering wheel and generates a SWA 142 based on the position of the steering wheel. As an example, the steering control module 140 may control vehicle steering via an EPS motor 144 based on the SWA 142. However, the vehicle may include another type of steering system. An electronic brake control module (EBCM) 150 may selectively control brakes 154 of the vehicle.

Modules of the vehicle may share parameters via a network 162, such as a controller area network (CAN). In vehicles, CAN may also stand for car area network. The network 162 may include one or more data buses. Various parameters may be made available by a given control module to other control modules via the network 162.

The driver inputs may include, for example, an accelerator pedal position (APP) 166 which may be provided to the ECM 106. A brake pedal position (BPP) 170 may be provided to the EBCM 150. A position 174 of a range selector, such as a park, reverse, neutral, drive lever (PRNDL), may be provided to the TCM 114. An ignition state 178 may be provided to a body control module (BCM) 180. For example, the ignition state 178 may be input by a driver via an ignition key, button, or switch. At a given time, the ignition state 178 may be one of off, accessory, run, or crank.

The vehicle system also includes an infotainment module 182. The infotainment module 182 controls what is displayed on a display 184. The display 184 may be a touchscreen display in various implementations and transmit signals indicative of user input to the display 184 to the infotainment module 182. The Infotainment module 182 may additionally or alternatively receive signals indicative of user input from one or more other user input devices 185, such as one or more switches, buttons, knobs, etc.

The infotainment module 182 may also generate output via one or more other devices. For example, the infotainment module 182 may output sound via one or more speakers 190 of the vehicle. The vehicle may include one or more additional control modules that are not shown, such as a chassis control module, a battery pack control module, etc. The vehicle may omit one or more of the control modules shown and discussed.

The vehicle also includes a pedestrian protection module 192 and a pedestrian protection system. As discussed further below, the pedestrian protection module 192 controls and diagnoses the pedestrian protection system.

Figure 2:
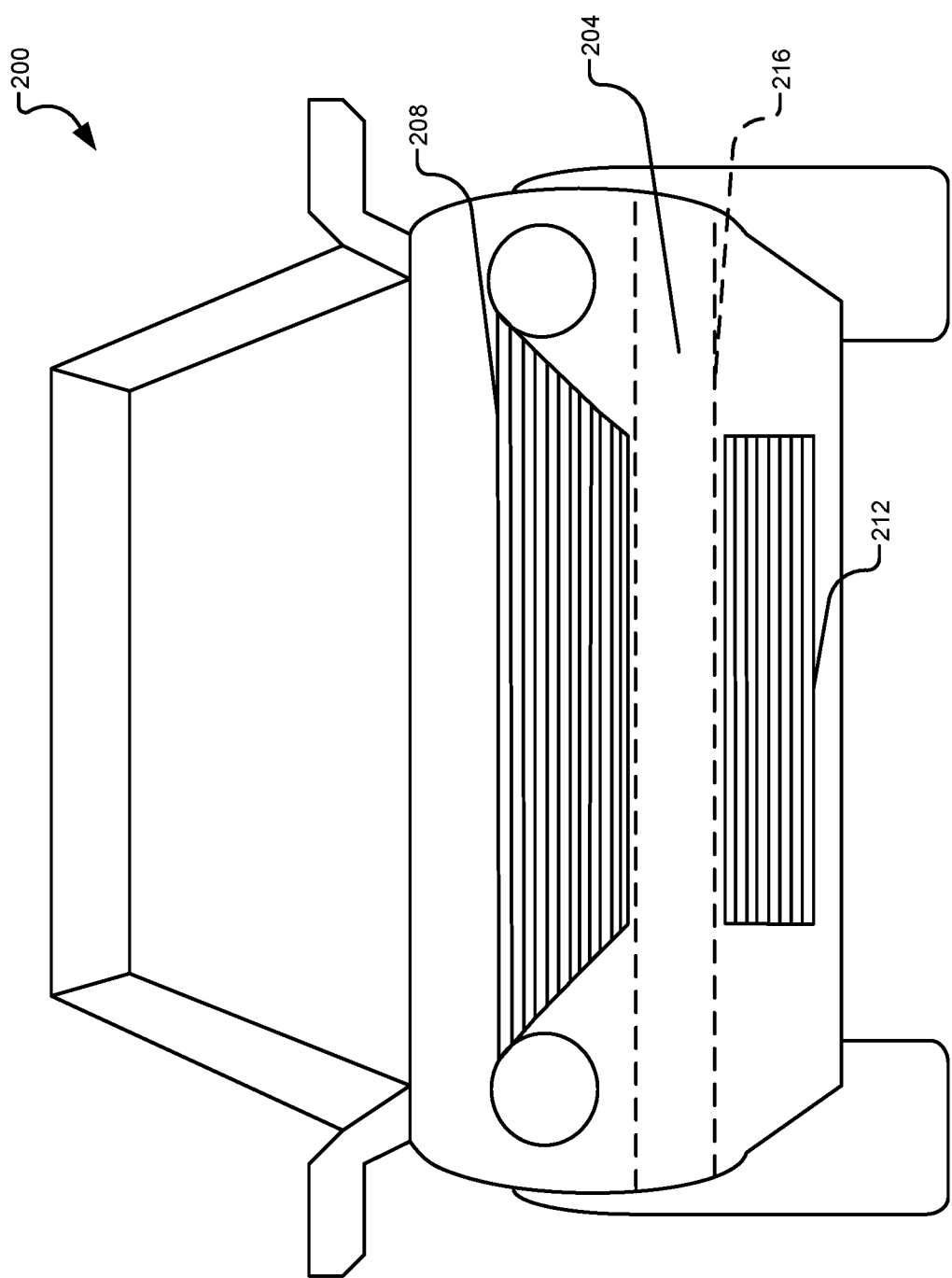
FIG. 2 is a functional block diagram of a front view of a vehicle including an example pedestrian protection system.

FIG. 2 includes a front view of an example vehicle 200 with a pedestrian protection system 216. The vehicle includes a front bumper fascia 204, an upper grille 208, and a lower grille 212. In various implementations, the upper grille 208 and/or the lower grille 212 may be omitted. The pedestrian protection system 216 is located behind the front bumper fascia 204 and may be between the upper grille 208 and the lower grille 212 of the vehicle 200.

Figure 3:
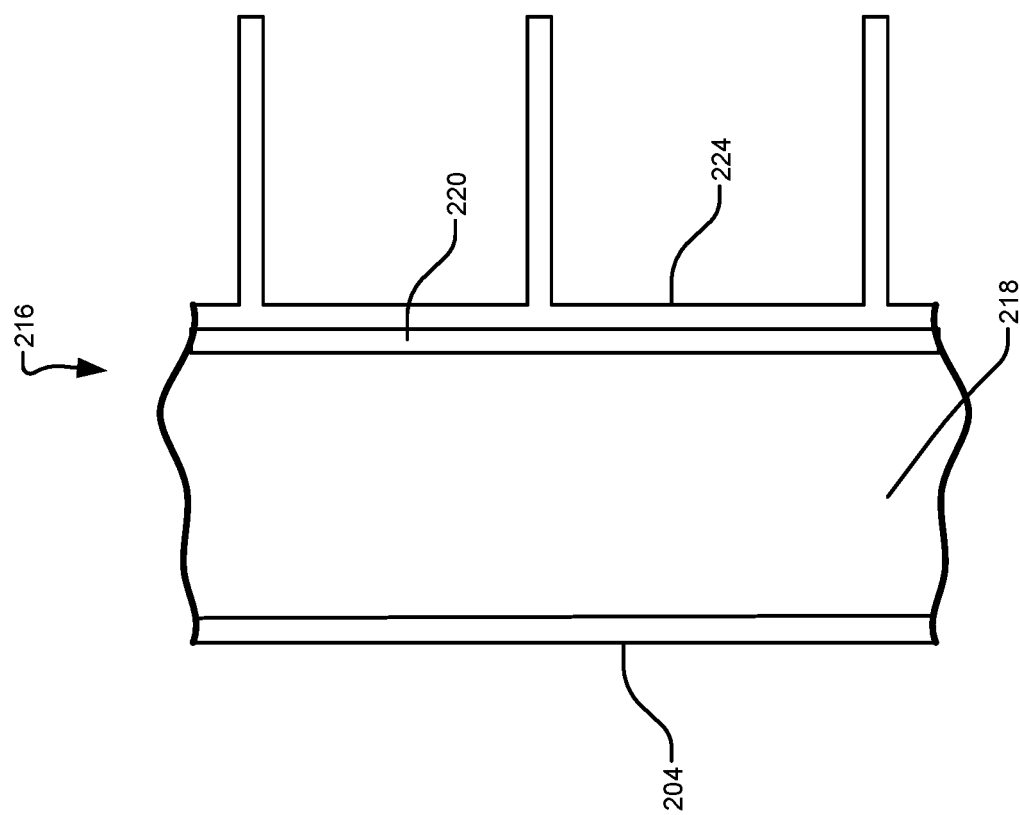
FIG. 3 is a cross sectional view including an example front bumper fascia, an energy absorber, a sensing tube, and a front bumper reinforcement.

FIG. 3 is a cross-sectional view including an example portion of the front bumper fascia 204, the pedestrian protection system 216, and a front bumper reinforcement 224. The pedestrian protection system 216 includes an energy absorber (e.g., an energy absorbing foam block) 218 and a sensing tube 220. The front bumper reinforcement 224 is attached to a chassis of the vehicle 200.

The energy absorber 218 may be sandwiched between the front bumper fascia 204 and the front bumper reinforcement 224. The sensing tube 220 may be embedded within the energy absorber 218 or located within a recess in the energy absorber 218.

Figure 4:
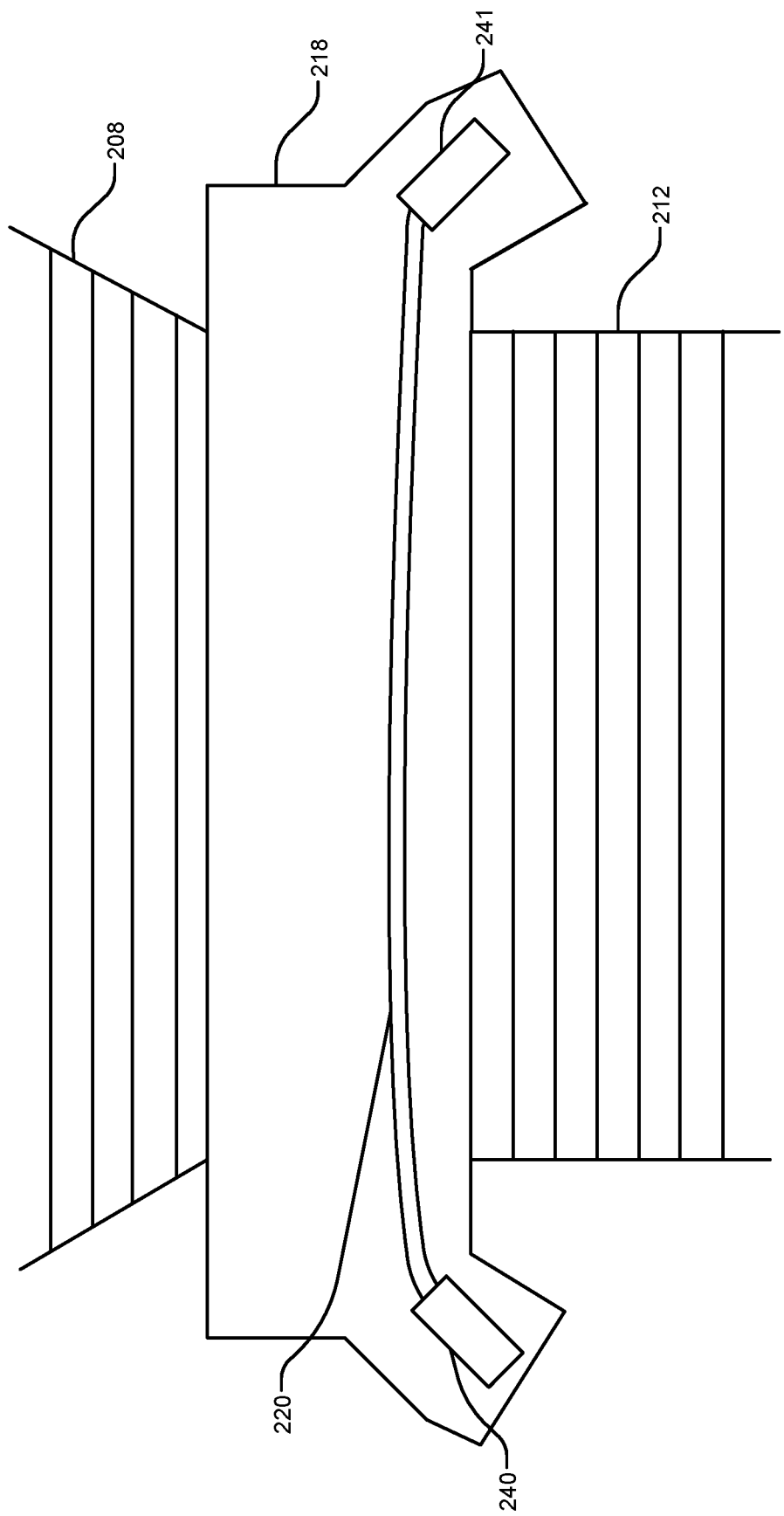
FIG. 4 is a view including an example pedestrian protection system.

FIG. 4 is a view of the pedestrian protection system 216 from a point of view behind (more rearward) the pedestrian protection system 216. The pedestrian protection system 216 also includes a first pressure sensor 240, and a second pressure sensor 241. The first pressure sensor 240 is connected to and measured a first pressure at a first end of the sensing tube 220. The second pressure sensor 241 is connected to and measured a second pressure at a second end of the sensing tube 220. The sensing tube 220 includes one or more vent holes that allow the pressure of the sensing tube 220 to approach or reach atmospheric/ambient pressure. In various implementations, the vent hole(s) may be through at least one of the first and second pressure sensors 240 and 241.

FIG. 5 includes an example exploded view of the pedestrian protection system 216. The energy absorber 218 has a front side 242 and a back side 243. The front side 242 faces and may be mounted to (the inner surface of) the front bumper fascia 204. The back side 243 faces and may be mounted to the front bumper reinforcement 224.

The sensing tube 220 may be located in a recess in the back side 243 of the energy absorber 218 such that a portion of the sensing tube 220 is exposed to the front bumper reinforcement 224. The first and second pressure sensors 240 and 241 may also be located in the recess in the back side 243 of the energy absorber 218. A collision with the front bumper fascia 204 compresses the energy absorber 218 and the sensing tube 220 against the front bumper reinforcement 224. Therefore, an internal volume of the sensing tube 220 decreases and pressure within the sensing tube 220 increases when a collision occurs.

The pressure increase may vary based upon what collides with the front bumper fascia 204. For example, a collision with a pedestrian may generate at least a 25 millibar pressure increase. A collision with a vehicle or another type of object, however, may generate a larger pressure increase.

Figure 6A:
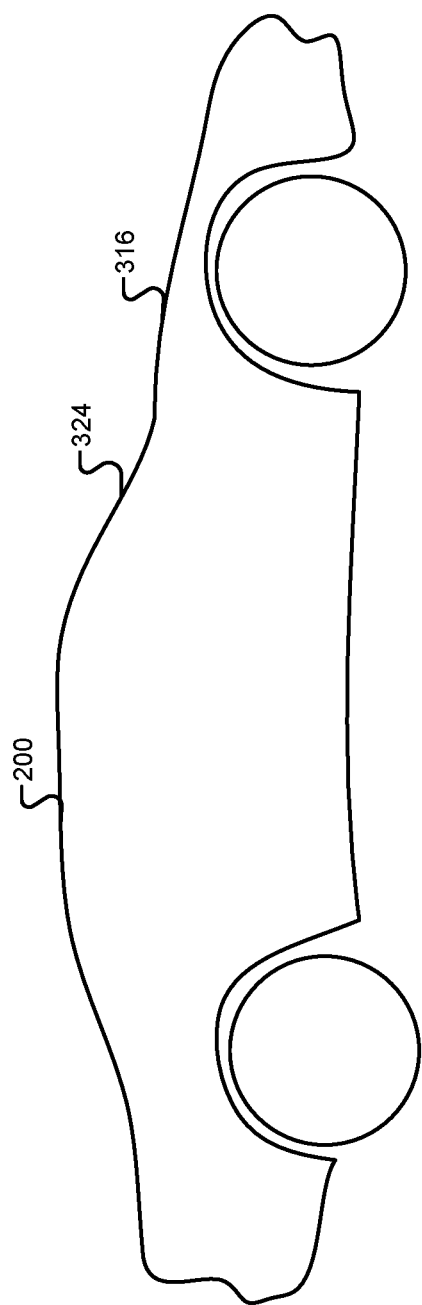
FIGS. 6A and 6B include side views of a vehicle including a pedestrian protection system before and after a collision with a pedestrian.
Figure 6B:
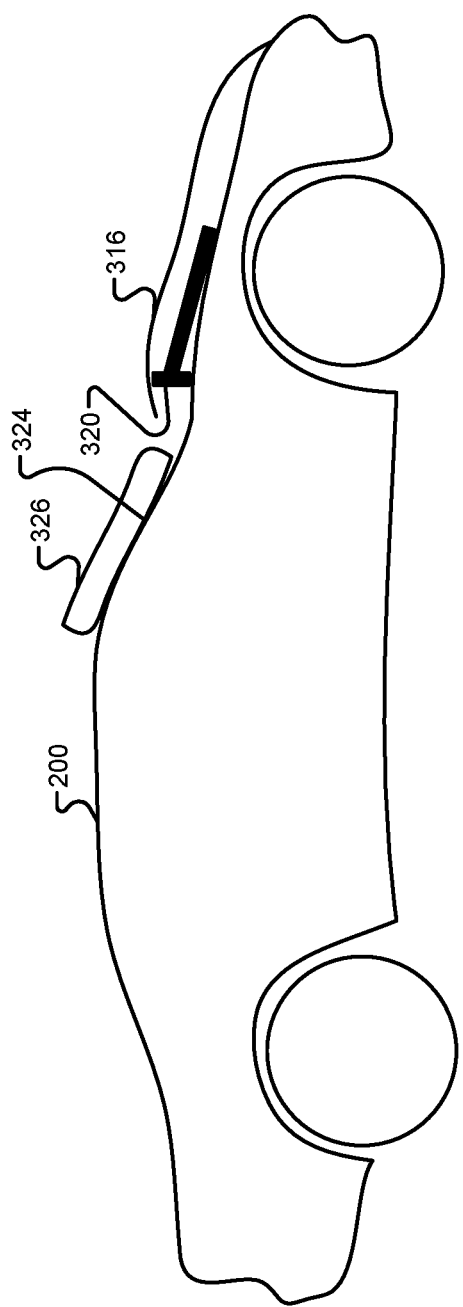

FIG. 6A includes an example side view of the vehicle 200 before a collision with a pedestrian. FIG. 6 includes an example side view of the vehicle 200 after a collision with a pedestrian.

The pedestrian protection module 192 actuates one or more actuators when a collision of the front bumper fascia 204 with a pedestrian is detected. For example, the pedestrian protection module 192 may actuate one or more hood lift actuators 320 when a collision of the front bumper fascia 204 with a pedestrian is detected. The one or more hood lift actuators 320 actuate and lift a rear portion of a hood 316 of the vehicle 200. The one or more hood lift actuators 320 may lift the rear portion of the hood 316, for example, to create a space between the hood 316 and components located under the hood 316. The one or more hood lift actuators 320 may be pyrotechnic actuators, linear actuators, or another suitable type of actuator. Additionally or alternatively, the pedestrian protection module 192 may deploy one or more windshield airbags 326 when a collision of the front bumper fascia 204 with a pedestrian is detected. The windshield airbag(s) 326 may be deployed, for example, to cover an outer surface of a front windshield 324 of the vehicle.

Figure 7:
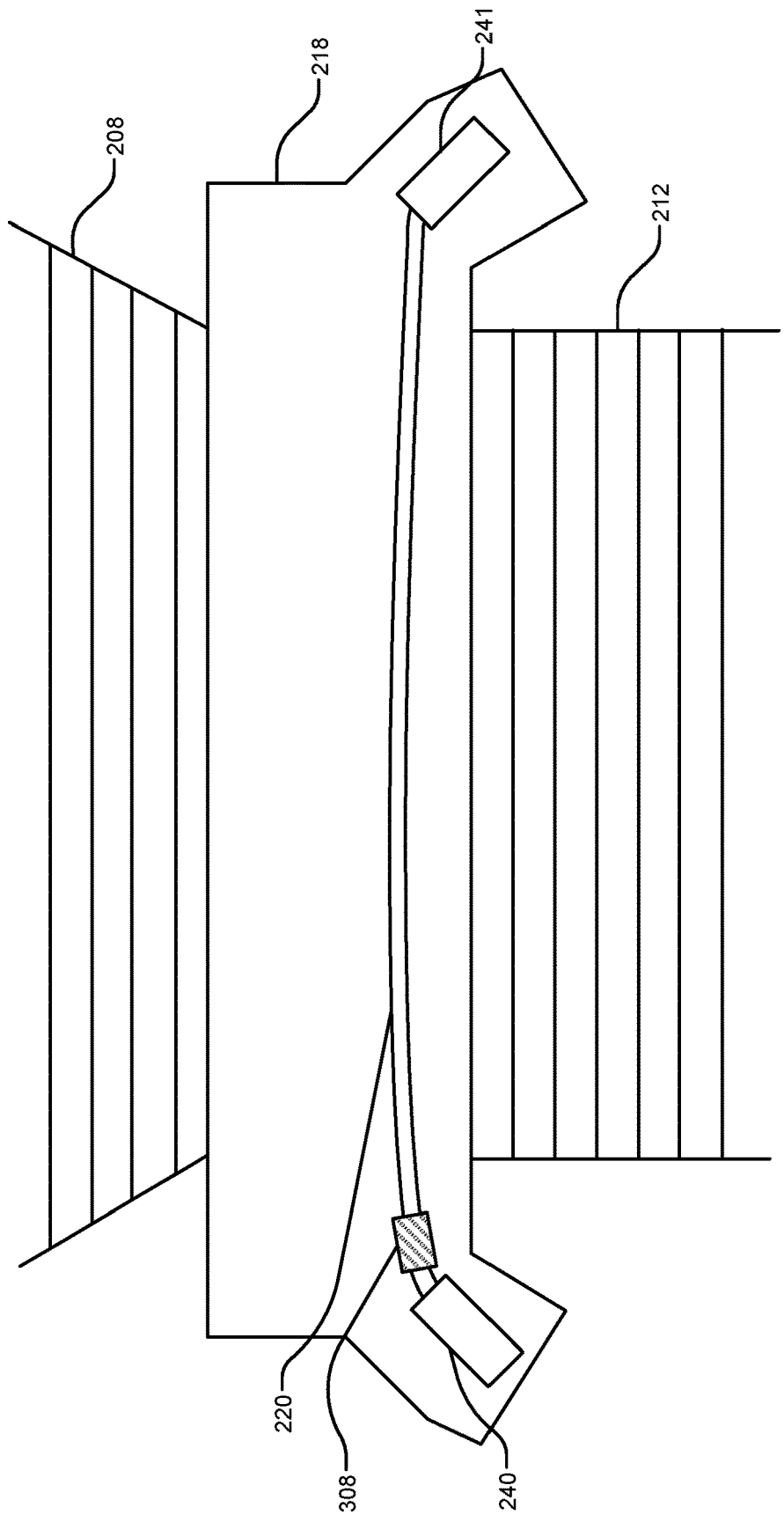
FIGS. 7-9 are functional block diagrams of example pedestrian protection systems.
Figure 8:
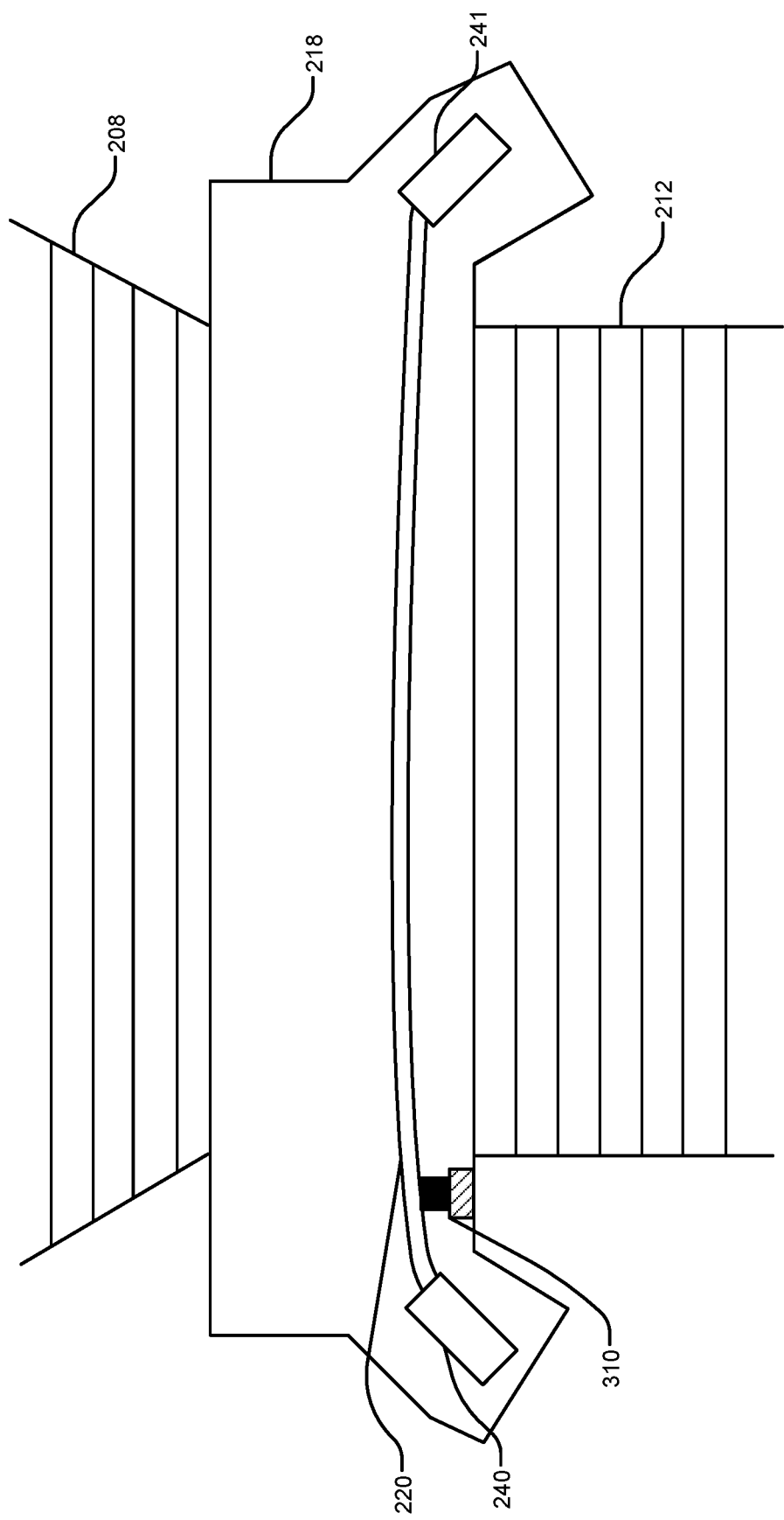
Figure 9:
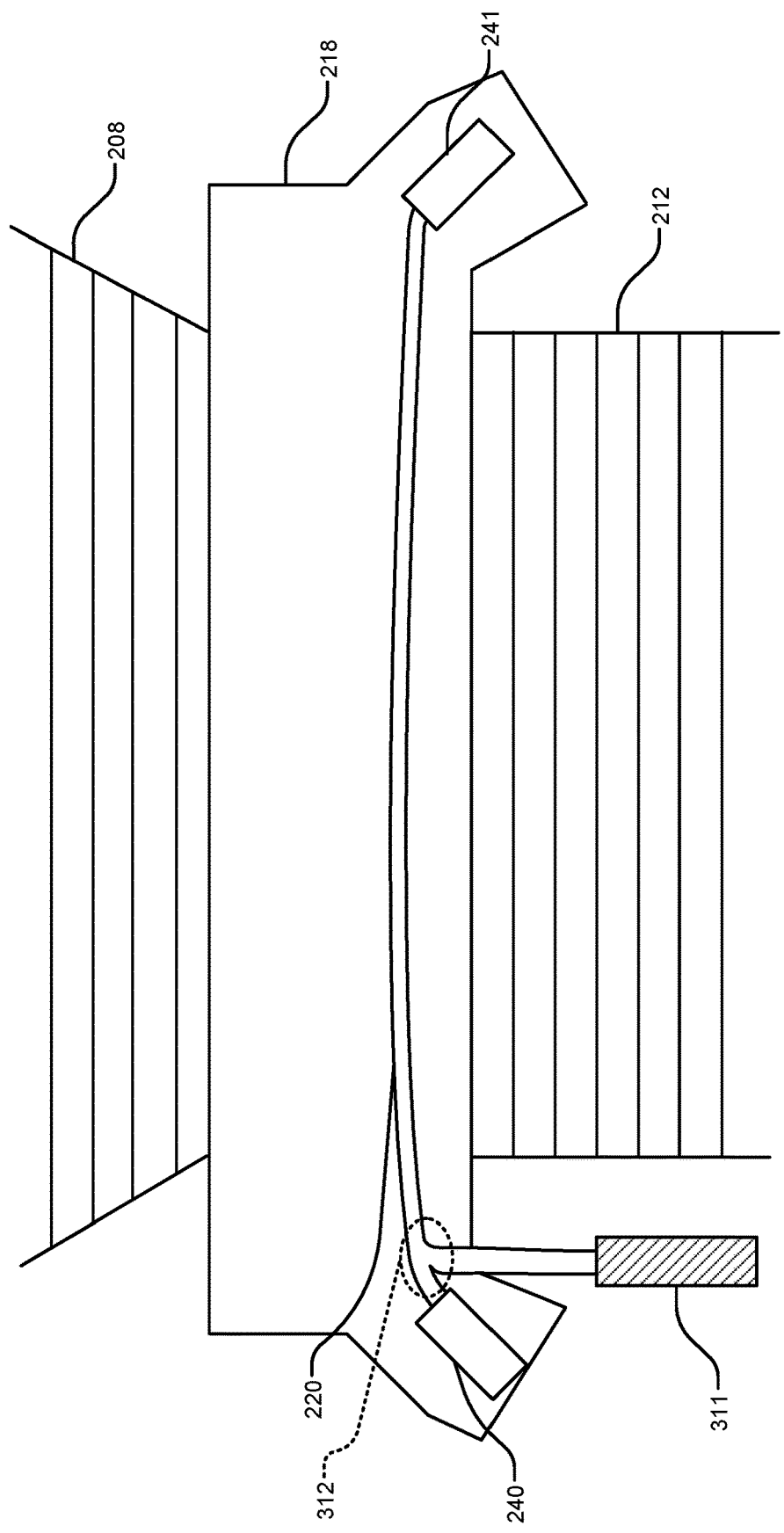

FIGS. 7-9 include functional block diagrams of example implementations of the pedestrian protection system 216. The pedestrian protection system 216 also includes an actuator. The pedestrian protection module 192 applies power to the actuator to actuate the actuator and increase pressure within the sensing tube 220. The pedestrian protection module 192 may apply power to the actuator, for example, from one or more batteries of the vehicle.

In FIG. 7, the actuator is shown as a piezoelectric actuator 308. The piezoelectric actuator 308 (e.g., circumferentially) wraps around the sensing tube 220. When the pedestrian protection module 192 applies power to the piezoelectric actuator 308, the piezoelectric actuator 308 constricts and causes a pressure increase within the sensing tube 220. In various implementations, the piezoelectric actuator 308 may be embedded within the walls of the sensing tube 220. The piezoelectric actuator 308 may be a ceramic tube actuator, a wire (e.g., nitinol wire) actuator, or another suitable type of tube actuator.

In FIG. 8, the actuator is shown as a first linear actuator 310. When the pedestrian protection module 192 applies power to the first linear actuator 310, the first linear actuator 310 extends into a side of the sensing tube 220 and causes a pressure increase within the sensing tube 220. In various implementations, the first linear actuator 310 may be located within the recess in the back side 243 of the energy absorber 218.

In FIG. 9, the actuator is shown as a second linear actuator 311. A splitter (e.g., a y-type connector or a t-type connector) 312 may be implemented and allow for the second linear actuator 311 to be connected to the sensing tube 220 in addition to the first and second pressure sensors 240 and 241. When the pedestrian protection module 192 applies power to the second linear actuator 311, the second linear actuator 311 extends and causes a pressure increase within the sensing tube 220. For example, the second linear actuator 311 may include a piston and may be located in line with or within the sensing tube 220. When power is applied to the second linear actuator 311, the second linear actuator 311 may extend the piston within the sensing tube 220 to increase the pressure within the sensing tube 220.

As discussed above, however, the sensing tube 220 may be damaged or at least one of the first and second pressure sensors 240 and 241 may be disconnected from the sensing tube 220. The pedestrian protection module 192 therefore selectively actuates the actuator to increase pressure within the sensing tube 220 to diagnose whether a fault is present in the sensing tube 220. The fault may be, for example, damage (e.g., puncturing or severing) of the sensing tube 220 or disconnection of at least one of the first and second pressure sensors 240 and 241 from the sensing tube 220. When the fault is present, at least one of the first and second pressure sensors 240 and 241 may not measure a pressure increase in response to the actuation of the actuator or may measure a pressure increase that is less than a predetermined pressure in response to the actuation of the actuator. When the fault is not present, the first and second pressure sensors 240 and 241 both measure increases of at least the predetermined pressure. While the example of the actuation increasing the pressure within the sensing tube 220 is provided, the actuator may alternatively actuate to decrease the pressure within the sensing tube 220.

Figure 10:
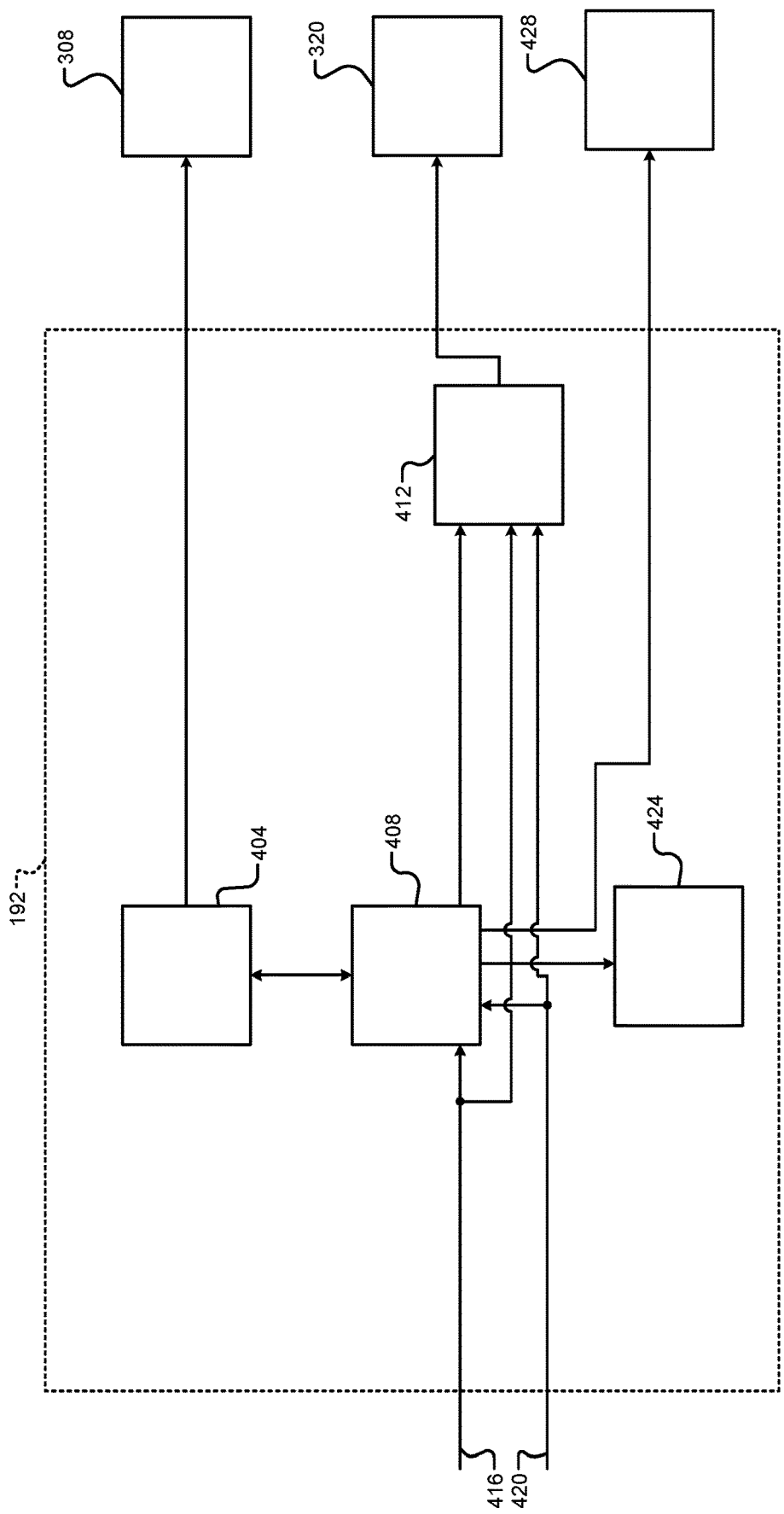
FIG. 10 includes a functional block diagram of an example implementation of a pedestrian protection module.

With reference to FIG. 10, a functional block diagram of an example implementation of the pedestrian protection module 192 is shown. The pedestrian protection module 192 includes a pressure changing module 404, a diagnostic module 408, and an actuator control module 412.

The actuator control module 412 selectively actuates the actuator(s), such as the hood lift actuator(s) 320, when a collision of the front bumper fascia 204 and a pedestrian are detected. The actuator control module 412 detects a collision of the front bumper fascia 204 and a pedestrian based on at least one of a first pressure 416 measured by the first pressure sensor 240 and a second pressure 420 measured by the second pressure sensor 241. For example, the actuator control module 412 may detect the occurrence of a collision of the front bumper fascia 204 and a pedestrian when at least one of the first pressure 416 increases and the second pressure 420 increases by at least a first predetermined pressure within a predetermined period. The first predetermined pressure may be, for example, approximately 25 millibar or another suitable pressure. The first predetermined pressure is less than a second predetermined pressure indicative of a collision of the front bumper fascia 204 with another object or vehicle.

The diagnostic module 408 selectively diagnoses whether the fault is present in the sensing tube 220. The diagnostic module 408 may diagnose whether the fault is present in the sensing tube 220 once per key cycle of the vehicle, such as each time the ignition state 178 is transitions to run. Before diagnosing whether the fault is present in the sensing tube 220, the diagnostic module 408 may verify that the first and second pressures 416 and 420 are within a predetermined amount (e.g., percentages or pressures) of an ambient air pressure measured by an ambient air pressure sensor. The diagnostic module 408 may also verify that no faults have been diagnosed in the first and second pressure sensors 240 and 241 before diagnosing whether the fault is present in the sensing tube 220.

When one or more faults have been diagnosed in the first in and second pressure sensors 240 and 241, the diagnostic module 408 may disable performance of the diagnostic of the sensing tube 220. When the first and second pressures 416 and 420 are not within the predetermined amount of the ambient air pressure measured, the diagnostic module 408 may disable performance of the diagnostic of the sensing tube 220. The diagnostic module 408 may also command the actuator control module 412 to disable actuation of the actuator(s) (e.g., the hood lift actuator(s) 320) when a collision of the front bumper fascia 204 and a pedestrian are detected.

The pressure changing module 404 actuates the actuator, such as the piezoelectric actuator 308, the first linear actuator 310, or the second linear actuator 311 for the diagnoses of whether the fault is present in the sensing tube 220. The diagnostic module 408 diagnoses whether the fault is present in the sensing tube 220 based on the first and second pressures 416 and 420 in response to actuation of the actuator.

For example, the diagnostic module 408 diagnoses that the fault is not present in the sensing tube 220 when the first pressure 416 and the second pressure 420 increase by a third predetermined pressure within a predetermined period after the actuation. The third predetermined pressure is less than the first predetermined pressure and may be, for example, approximately 5 millibar or another suitable pressure. The actuation of the actuator is configured to cause the first and second pressures 416 and 420 to increase by more than the third predetermined pressure but less than the first predetermined pressure. The diagnostic module 408 diagnoses that the fault is present in the sensing tube 220 when at least one of the first pressure 416 and the second pressure 420 does not increase by the third predetermined pressure within the predetermined period after the actuation.

The diagnostic module 408 takes one or more remedial actions when the fault is present in the sensing tube 220. For example, the diagnostic module 408 sets a predetermined diagnostic trouble code (DTC) in diagnostic memory 424 to a first state when the fault is present in the sensing tube 220. The diagnostic module 408 sets the predetermined DTC to a second state when the fault is not present in the sensing tube 220. The predetermined DTC is associated with the fault in the sensing tube 220. When the predetermined DTC is set to the first state, a service technician may be able to quickly determine that the sensing tube 220 is damaged and/or at least one of the first and second pressure sensors 240 and 241 are disconnected from the sensing tube 220.

Additionally or alternatively, the diagnostic module 408 may display or illuminate a malfunction indicator 428 when the fault is present in the sensing tube 220. The malfunction indicator 428 may be a malfunction indicator light (MIL) or a visual indicator, such as displayed on the display 184. Additionally or alternatively, when the fault is present in the sensing tube 220, the diagnostic module 408 may command the actuator control module 412 to disable actuation of the actuator(s) (e.g., the hood lift actuator(s) 320) when a collision of the front bumper fascia 204 and a pedestrian are detected.

Figure 11:
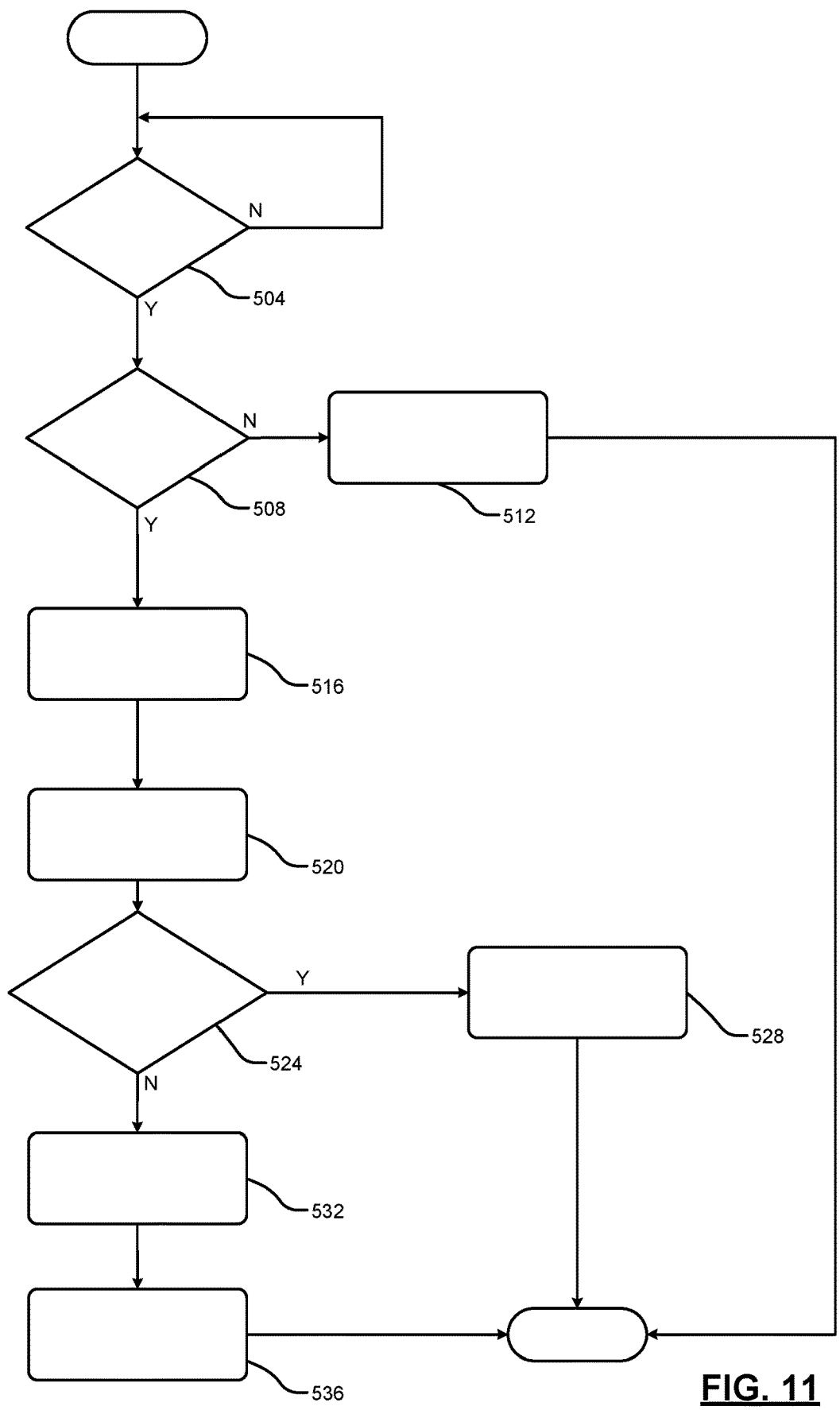
FIG. 11 is a flowchart depicting an example method of diagnosing a fault in a sensing tube.

FIG. 11 is a flowchart depicting an example method of diagnosing the presence of the fault in the sensing tube 220. Control may begin with 504 where the diagnostic module 408 may determine whether the ignition state 178 has transitioned to the run state. If 504 is true, control continues with 508. While the example of the ignition state 178 transitioning to the run state is provided, one or more other suitable enabling conditions may be used. If 504 is false, control may remain at 504.

At 508, the diagnostic module 408 may determine whether the first and second pressures 416 and 420 measured by the first and second pressure sensors 240 and 241, respectively, are within the predetermined amount of ambient/atmospheric air pressure. If 508 is true, control continues with 516. If 508 is false, at 512 the diagnostic module 408 may command the actuator control module 412 to disable actuation of the actuator(s) (e.g., the hood lift actuator(s) 320) when a collision of the front bumper fascia 204 and a pedestrian are detected.

At 516, the pressure changing module 404 actuates the actuator to increase the pressure within the sensing tube 220. For example, the pressure changing module 404 actuates the piezoelectric actuator 308, the first linear actuator 310, or the second linear actuator 311.

At 520, the diagnostic module 408 obtains new values of the first and second pressures 416 and 420 and determines first and second changes in the first and second pressures 416 and 420 (e.g., relative to their respective values at 508). At 524, the diagnostic module 408 determines whether the first and second changes in the first and second pressures 416 and 420 are greater than the third predetermined pressure. If 524 is true, at 528 the diagnostic module 408 indicates that the fault is not present in the sensing tube 220 (e.g., sets the predetermined DTC to the second state) and allows the actuator control module 412 to actuate of the actuator(s) (e.g., the hood lift actuator(s) 320) when a collision of the front bumper fascia 204 and a pedestrian are detected. If 524 is false, control continues with 532.

At 532, the diagnostic module 408 indicates that the fault is present in the sensing tube 220. For example, the diagnostic module 408 may set the predetermined DTC to the first state. The diagnostic module 408 may also take one or more remedial actions. For example, at 536 the diagnostic module 408 may display or illuminate the malfunction indicator 428 and/or command the actuator control module 412 disable actuation of the actuator(s) (e.g., the hood lift actuator(s) 320) when a collision of the front bumper fascia 204 and a pedestrian are detected. While control is shown as ending, control may return to 504.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules, circuit elements, semiconductor layers, etc.) are described using various terms, including "connected," "engaged," "coupled," "adjacent," "next to," "on top of," "above," "below," and "disposed." Unless explicitly described as being "direct," when a relationship between first and second elements is described in the above disclosure, that relationship can be a direct relationship where no other intervening elements are present between the first and second elements, but can also be an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A.

In this application, including the definitions below, the term "module" or the term "controller" may be replaced with the term "circuit." The term "module" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

The term code, as used above, may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks, flowchart components, and other elements described above serve as software specifications, which can be translated into the computer programs by the routine work of a skilled technician or programmer.

The computer programs include processor-executable instructions that are stored on at least one non-transitory, tangible computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation) (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

None of the elements recited in the claims are intended to be a means-plus-function element within the meaning of 35 U.S.C. § 112(f) unless an element is expressly recited using the phrase "means for," or in the case of a method claim using the phrases "operation for" or "step for."

What is claimed is:

1. A diagnostic system of a vehicle, comprising:
    an energy absorber sandwiched between a front bumper fascia and a front bumper reinforcement of the vehicle;
    a sensing tube located between a portion of the energy absorber and the front bumper reinforcement;
    a first pressure sensor that is connected to a first end of the sensing tube and that is configured to measure a first pressure of air within the sensing tube;
    a second pressure sensor that is connected to a second end of the sensing tube and that is configured to measure a second pressure of air within the sensing tube;
    an actuator configured to actuate and vary a pressure within the sensing tube;
    a diagnostic module configured to selectively diagnose the presence of a fault with the sensing tube based on at least one of:
        a first change in the first pressure in response to actuation of the actuator; and
        a second change in the second pressure in response to the actuation of the actuator.

2. The diagnostic system of claim 1 wherein the diagnostic module is configured to diagnose the presence of the fault with the sensing tube when at least one of:
    the first change in the first pressure in response to actuation of the actuator is less than a predetermined pressure; and
    the second change in the second pressure in response to the actuation of the actuator is less than the predetermined pressure.

3. The diagnostic system of claim 2 wherein the diagnostic module is configured to diagnose that the fault is not present with the sensing tube when both:

the first change in the first pressure in response to actuation of the actuator is greater than the predetermined pressure; and the second change in the second pressure in response to the actuation of the actuator is greater than the predetermined pressure.

4. The diagnostic system of claim 1 wherein the actuator comprises a piezoelectric tube actuator that surrounds a circumference of the sensing tube.

5. The diagnostic system of claim 1 wherein the actuator comprises a nitinol wire wrapped around a circumference of the sensing tube.

6. The diagnostic system of claim 1 wherein the actuator comprises a linear actuator that is configured to actuate and apply force to a side of the sensing tube.

7. The diagnostic system of claim 1 further comprising a splitter,
wherein the actuator comprises a linear actuator that includes a piston and that is connected to the splitter, and
wherein the linear actuator is configured to extend the piston within the sensing tube.

8. The diagnostic system of claim 1 wherein the sensing tube is located within a recess in the energy absorber.

9. The diagnostic system of claim 1 wherein the sensing tube is located within a recess formed in a face of the energy absorber that faces the front bumper reinforcement.

10. The diagnostic system of claim 1 wherein the first and second pressure sensors include holes venting the sensing tube to ambient air.

11. The diagnostic system of claim 1 further comprising an actuator control module configured to selectively lift a rear portion of a hood of the vehicle based on at least one of the first pressure measured by the first pressure sensor and the second pressure measured by the second pressure sensor.

12. The diagnostic system of claim 11 wherein the actuator control module is configured to disable the lifting of the rear portion of a hood of the vehicle when the fault is present with the sensing tube.

13. The diagnostic system of claim 11 wherein:
the diagnostic module is configured to diagnose that the fault is not present with the sensing tube when both:
a first change in the first pressure in response to actuation of the actuator is greater than a first predetermined pressure; and
a second change in the second pressure in response to the actuation of the actuator is greater than the first predetermined pressure; and
the actuator control module is configured to lift the rear portion of the hood when both:
a third change in the first pressure is greater than a second predetermined pressure; and
a fourth change in the second pressure in response to the actuation of the actuator is greater than the second predetermined pressure.

14. The diagnostic system of claim 13 wherein the second predetermined pressure is greater than the first predetermined pressure.

15. The diagnostic system of claim 13 wherein the diagnostic module is configured to diagnose that the fault is present with the sensing tube when at least one of:
the first change in the first pressure in response to actuation of the actuator is less than the first predetermined pressure; and
the second change in the second pressure in response to the actuation of the actuator is less than the first predetermined pressure.

16. The diagnostic system of claim 1 wherein the diagnostic module is configured to store a predetermined diagnostic trouble code in memory when the fault is present with the sensing tube.

17. The diagnostic system of claim 1 wherein the diagnostic module is configured to display a malfunction indicator on a display of the vehicle or to illuminate a malfunction indicator light when the fault is present with the sensing tube.

18. The diagnostic system of claim 1 wherein the actuator is configured to actuate and increase the pressure within the sensing tube.

19. A diagnostic method for a vehicle, comprising:
by a first pressure sensor, measuring a first pressure of air within a sensing tube,
wherein the sensing tube is located between a portion of an energy absorber and a front bumper reinforcement, and
wherein the energy absorber is sandwiched between a front bumper fascia and the front bumper reinforcement;
by a second pressure sensor, measuring a second pressure of air within the sensing tube;
actuating and actuator and varying a pressure within the sensing tube; and
selectively diagnosing the presence of a fault with the sensing tube based on at least one of:
a first change in the first pressure in response to actuation of the actuator; and
a second change in the second pressure in response to the actuation of the actuator.

20. A diagnostic system, comprising:
a sensing tube;
a first pressure sensor that is connected to a first end of the sensing tube and that is configured to measure a first pressure of air within the sensing tube;
a second pressure sensor that is connected to a second end of the sensing tube and that is configured to measure a second pressure of air within the sensing tube;
an actuator configured to actuate and vary a pressure within the sensing tube;
a diagnostic module configured to selectively diagnose the presence of a fault with the sensing tube based on at least one of:
a first change in the first pressure in response to actuation of the actuator; and
a second change in the second pressure in response to the actuation of the actuator.

\* \* \* \* \*